US00PP24502P3

(12) United States Plant Patent
Scheffers

(10) Patent No.: US PP24,502 P3
(45) Date of Patent: May 27, 2014

(54) *YUCCA* PLANT NAMED 'YUGOSTA02'

(50) Latin Name: *Yucca guatemalensis*
Varietal Denomination: Yugosta02

(75) Inventor: Ruud Scheffers, Honselersdijk (NL)

(73) Assignee: Dragontree Beheer B.U. (NL)

( * ) Notice: Subject to any disclaimer, the term of this patent is extended or adjusted under 35 U.S.C. 154(b) by 177 days.

(21) Appl. No.: 13/507,152

(22) Filed: Jun. 7, 2012

(65) Prior Publication Data

US 2013/0333082 P1 Dec. 12, 2013

(51) Int. Cl.
*A01H 5/00* (2006.01)

(52) U.S. Cl.
USPC ..... Plt./373

(58) Field of Classification Search
USPC ..... Plt./373, 263.1
See application file for complete search history.

*Primary Examiner* — Kent L Bell
(74) *Attorney, Agent, or Firm* — Cassandra Bright

(57) ABSTRACT

A new and distinct *Yucca* cultivar named 'Yugosta02' is disclosed, characterized by green margins and a lighter interior foliage coloration. The new variety is a *Yucca*, typically produced as an ornamental plant.

1 Drawing Sheet

Latin name of the genus and species: *Yucca guatemalensis*.
Variety denomination: 'Yugosta02'.

BACKGROUND OF THE INVENTION

The new cultivar is the product of chance discovery. The new variety originated as a naturally occurring mutation of an unpatented, variety *Yucca guatemalensis* 'Silver Star'.

The new variety was discovered by the inventor, Ruud A. M. Scheffers, a citizen of the Netherlands, in July of 2009 in a commercial greenhouse belonging to the inventor in Honselersdijk, The Netherlands. After identifying the new variety as a potentially interesting selection, the inventor continued confidential testing and propagation of 'Yugosta02' assessing stability of the unique characteristics of this variety.

Asexual reproduction of the new cultivar 'Yugosta02' was first performed at the commercial greenhouse of the inventor in Honselersdijk, The Netherlands by vegetative cuttings in July of 2009. Access to all plants was restricted, as plants were kept in a locked greenhouse not open to the public. Through subsequent propagation by vegetative cuttings, multiple generations have been reproduced, which have shown that the unique features of this cultivar are stable and reproduced true to type.

SUMMARY OF THE INVENTION

The cultivar 'Yugosta02' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Yugosta02'. These characteristics in combination distinguish 'Yugosta02' as a new and distinct *Yucca* cultivar:

1. Variegated leaves, with green margins and lighter colored interior.

PARENT COMPARISON

Plants of the new cultivar 'Yugosta02' are similar to the parent, *Yucca guatemalensis* 'Silver Star' in most horticultural characteristics. The new variety, however, produces leaves with a different color of margin compared to those of the parent.

COMMERCIAL COMPARISON

'Yugosta02' is in plant habit, and other horticultural characteristics most similar to the parent variety.

BRIEF DESCRIPTION OF THE PHOTOGRAPH

The accompanying photograph in FIG. 1 illustrates in full color a typical plant of 'Yugosta02' grown in a commercial greenhouse in Honselersdijk, The Netherlands. This plant is approximately 48 months old, shown planted in a 5 liter container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'Yugosta02' plants grown in a greenhouse in Honselersdijk, The Netherlands. A steady temperature of approximately 20° C. at night and 20° C. during the day was maintained. No artificial light, photoperiodic treatments were given to the plants. Measurements and numerical values represent averages of typical plant types.

Botanical classification: *Yucca guatemalensis* 'Yugosta02'.

PROPAGATION

Time to initiate rooting: About 42 days at approximately 20° C.

Root description: Moderately thick, moderately fibrous, not fleshy, young roots white, near RHS 155A; older roots greyed-orange, near 171B.

PLANT

Age of the plant described: Approximately 48 months.
Growth habit: Upright.
Height: Average: 67.5 cm.
Plant spread: Average: 70.0 cm.
Normal pot size: 17 cm pots and larger.
Growth rate: Moderate; average growth (in spring), approx. 5 cm per month.
Stem characteristics:
*Length*.—Approximately 37.5 cm.
*Diameter*.—Approximately 2.6 cm.
*Aspect*.—Approximately 90° angle (near vertical).
*Strength*.—Very strong.
*Texture*.—Glabrous, slightly glossy, covered with leaf-scars.
*Color*.—Near RHS 172B to 175A, older stems near RHS 177B to 200D, leaf-scars near RHS NN155A to 156D.

FOLIAGE

Leaf:
*Arrangement*.—Alternate, spirally placed on main stem.
*Quantity per plant*.—Average: 23.
*Average length*.—Approximately 41.5 cm.
*Average width*.—Approximately 3.8 cm.
*Shape of blade*.—Ensiform.
*Aspect*.—Outward, in an average angle of 40° (0°=horizontal).
*Apex*.—Long and narrow apiculate, sharp to the touch.
*Base*.—Cuneate, sheathing. Sheathing? Yes. Sheath length: Average 2.5 cm. Sheath width: Average 2.7 cm. Sheath color: Upper side near RHS 145D, under side near RHS 145B to 144A, margins darker, near RHS 143A.
*Margin*.—Finely toothed, sharp to the touch; teeth slightly pointed towards the apex, therefore less sharp when rubbed from apex towards base of leaf.
*Texture of top surface*.—Smooth, glabrous, slightly glossy.
*Texture of bottom surface*.—Smooth, glabrous, dull, mid-section moderately rough to the touch.
*Color*.—Young foliage upper side: Margins (average width 0.6 cm) near RHS 137A and 146A, mid section lighter, near RHS 138B, 144B, 145B, 145C and 154D. All colors individually present. Young foliage under side: Margins (average width 0.6 cm) near RHS 137A and 137B, mid section lighter, near RHS 148D, 150C and 154C. All colors individually present. Mature foliage upper side: Margins (average width 1.1 cm) near RHS N137A and 139A, mid section lighter, near RHS 158D, N189C and 189D. All colors individually present. Mature foliage under side: Margins (average width 1.1 cm) near RHS N137A and N137B, mid section near RHS 150D, 158D and N189D. All colors individually present.
*Venation*.—Type: Parallel. Venation coloration: Indistinguishable from leaf blade.

OTHER CHARACTERISTICS

Flower production: Not observed.
Disease/pests resistance: Neither resistance nor susceptibility to normal diseases and pests of *Yucca* has been observed.
Drought tolerance and temperature tolerance: Moderately high drought resistance, good heat resistance.
Fruit/seed production: Not observed.

What is claimed is:

1. A new and distinct cultivar of *Yucca* plant named 'Yugosta02' as herein illustrated and described.

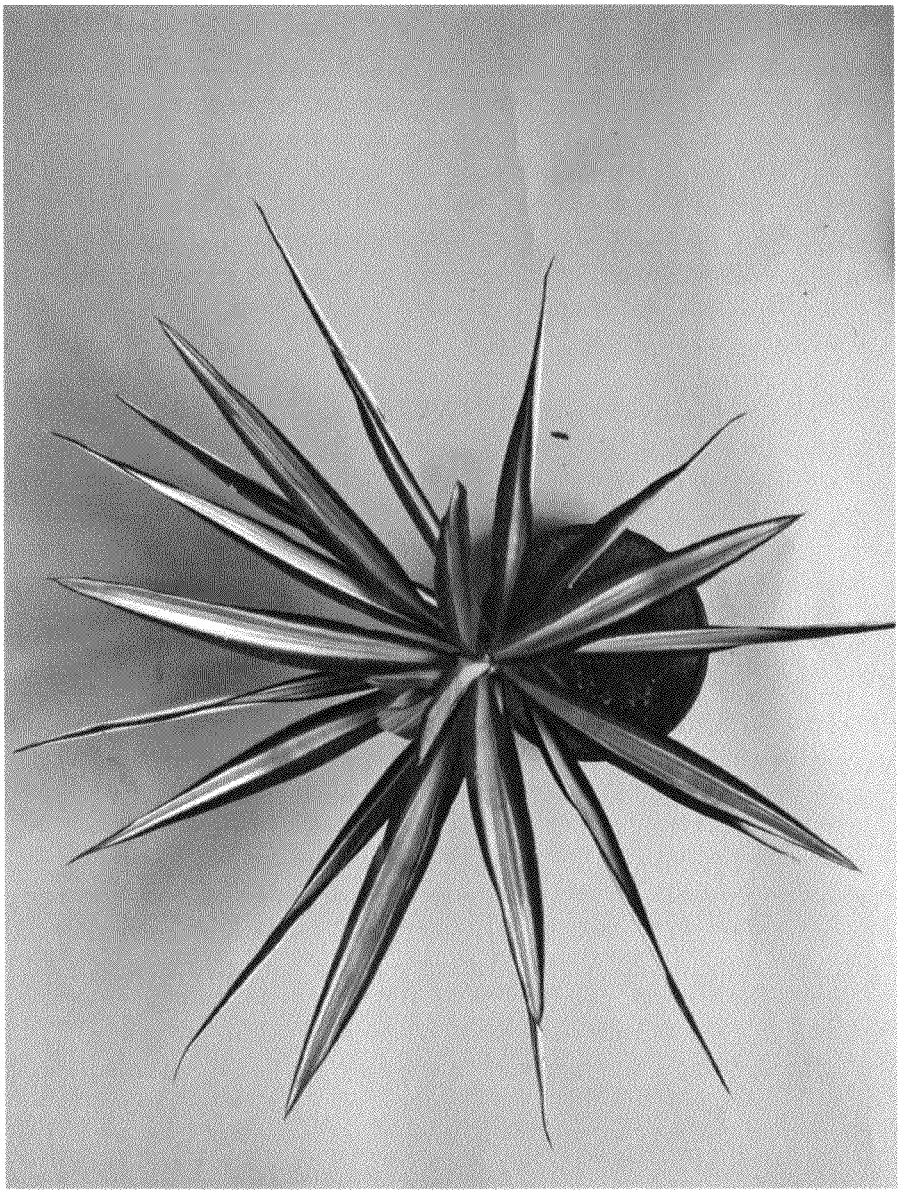

* * * * *